US00PP30239P2

(12) United States Plant Patent
Head

(10) Patent No.: US PP30,239 P2
(45) Date of Patent: Feb. 26, 2019

(54) ***GARDENIA* PLANT NAMED 'WAH-LM'**

(50) Latin Name: *Gardenia jasminoides*
Varietal Denomination: WAH-LM

(71) Applicant: William A. Head, Seneca, SC (US)

(72) Inventor: William A. Head, Seneca, SC (US)

(73) Assignee: Southern Plant Group, Marietta, GA (US)

( * ) Notice: Subject to any disclaimer, the term of this patent is extended or adjusted under 35 U.S.C. 154(b) by 23 days.

(21) Appl. No.: 15/732,055

(22) Filed: Sep. 12, 2017

(51) Int. Cl.
*A01H 5/02* (2018.01)

(52) U.S. Cl.
USPC ..... Plt./255
CPC ..... *A01H 5/02* (2013.01)

(58) Field of Classification Search
USPC ..... Plt./255
See application file for complete search history.

*Primary Examiner* — Anne Marie Grunberg
(74) *Attorney, Agent, or Firm* — Audrey Charles

(57) ABSTRACT

A new and distinct cultivar of *Gardenia* plant named 'WAH-LM', characterized by its fragrant, single-type, white-colored inflorescences, glossy, dark green-colored foliage, and moderately vigorous, compact-mounded growth habit, is disclosed.

1 Drawing Sheet

Latin name of genus and species of plant claimed: *Gardenia jasminoides.*

Variety denomination: 'WAH-LM'.

BACKGROUND OF THE INVENTION

The present invention relates to a new and distinct cultivar of *Gardenia* plant botanically known as *Gardenia jasminoides* and hereinafter referred to by the cultivar name 'WAH-LM'.

The new cultivar originated in a controlled breeding program in Seneca, S.C. during the spring of 2008. The objective of the breeding program was the development of *Gardenia* cultivars that have increased cold hardiness and root rot resistance.

The new *Gardenia* cultivar is the result of open-pollination. The female (seed) parent of the new cultivar is 'Daisy', not patented, characterized by its white-colored inflorescences, dark green-colored foliage, and moderately vigorous, upright to mounded habit. The male (pollen) parent of the new cultivar is unknown. The new cultivar was discovered and selected as a single flowering plant within the progeny of the above stated open-pollination during the summer of 2009 in a controlled environment in Seneca, S.C.

Asexual reproduction of the new cultivar by softwood cuttings since the summer of 2014 in Seneca, S.C. and Hickory, N.C. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'WAH-LM' as a new and distinct cultivar of *Gardenia* plant:

1. Fragrant, single-type, white-colored inflorescences;
2. Glossy, dark green-colored foliage; and
3. Moderately vigorous, compact-mounded growth habit.

Plants of the new cultivar differ from plants of the female parent primarily in having a more spreading habit, smaller leaves, and earlier seasonal flowering with more flowers per plant.

Of the many commercially available *Gardenia* cultivars, the most similar in comparison to the new cultivar is 'Radicans', not patented. However, in comparison, plants of the new cultivar differ from plants of 'Radicans' in at least the following characteristics:

1. Plants of the new cultivar have fewer flower petals than plants of 'Radicans';
2. Plants of the new cultivar are more cold hardy than plants of 'Radicans'; and
3. Plants of the new cultivar are wider than plants of 'Radicans'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'WAH-LM'. The plants were grown in 3-gallon containers for approximately 2 years in an outdoor nursery in West Grove, Pa. For the final two months of growth, the plants were moved during the winter season to greenhouse conditions to force flowering.

DETAILED BOTANICAL DESCRIPTION

Figure 1:
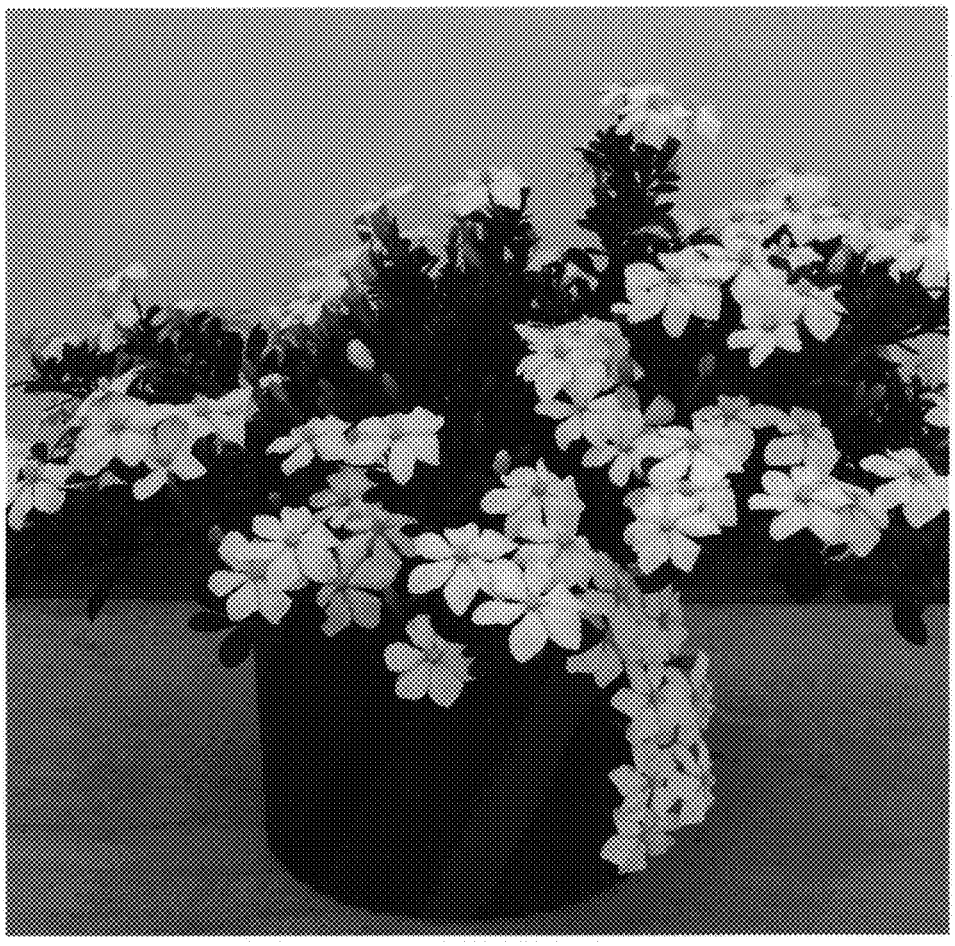
FIG. 1 illustrates a side view of the overall growth and flowering habit of 'WAH-LM'.
Figure 2:
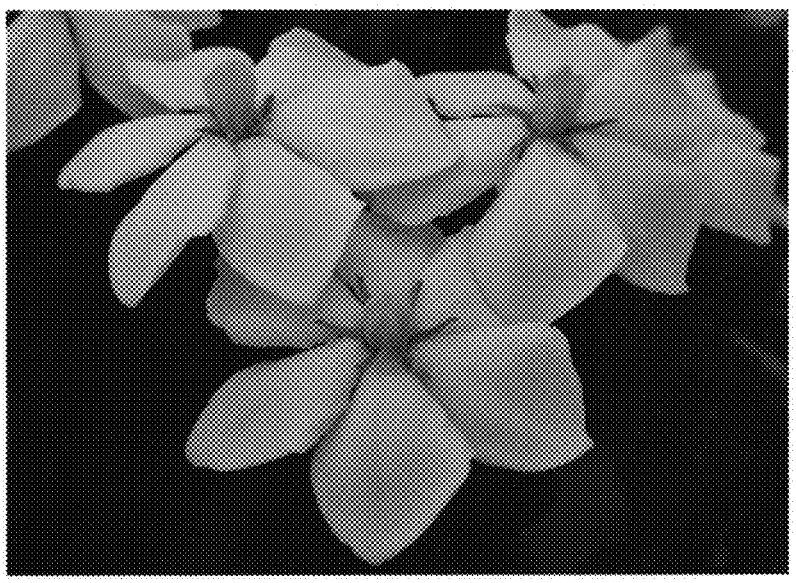
FIG. 2 illustrates a close-up view of a flower cluster of 'WAH-LM'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in February 2017 under natural light conditions in West Grove, Pa.

The following descriptions and measurements describe plants produced from cuttings from stock plants. The plants were grown in 3-gallon containers utilizing a soilless growth medium for approximately 2 years in an outdoor nursery in West Grove, Pa. During winter, the plants were moved for the final two months of growth to greenhouse conditions to force flowering. Greenhouse temperatures were maintained at 74° F. to 80° F. (23° C. to 27° C.) during the day and approximately 66° F. to 70° F. (19° C. to 21° C.) during the night. Greenhouse light levels of 2,200 footcandles to 3,100 footcandles were maintained during the day. Measurements and numerical values represent averages of typical plants.

Botanical classification: *Gardenia jasminoides* 'WAH-LM'.

Parentage:

*Female parent*.—'Daisy', not patented.

*Male parent*.—Unknown.

Propagation:

*Type cutting*.—Softwood cuttings.

*Time to initiate roots during the summer*.—Approximately 42 days.

*Time to produce a rooted cutting during the summer*.—Approximately 70 days.

*Root description*.—Medium in thickness, fleshy, white to brown in color.

*Rooting habit*.—Moderately branching, medium density.

Plant description:

*Commercial crop time*.—Approximately one year from a rooted cutting to finish in a 3-gallon container.

*Growth habit and general appearance*.—Moderately vigorous, compact-mounded growth habit.

*Hardiness*.—USDA Zone 7 (0° F. to 10° F.).

*Heat tolerance*.—Regularly tolerates temperatures as high as 40° C. in the summer.

*Size*.—Height from soil level to top of plant plane: Approximately 28.0 cm. Width: Approximately 70.0 cm.

*Branching habit*.—Freely branching. Pinching enhances branching. Quantity of lateral branches per plant: Approximately 12.

*Branch*.—Strength: Strong. Length: Approximately 12.0 cm to 17.0 cm. Diameter: Approximately 4.0 mm. Length of central internode: Approximately 2.0 cm. Texture: Densely glandular pubescent. Gland color: Colorless, transparent. Color of young and mature stems: 137C.

Foliage description:

*General description*.—Fragrance: None detected. Form: Simple. Arrangement: Opposite.

*Leaves*.—Shape: Elliptic. Margin: Entire. Apex: Rounded. Base: Aequilateral. Venation pattern: Pinnate. Length of mature leaf: Approximately 2.5 cm. Width of mature leaf: Approximately 1.0 cm. Texture of upper and lower surfaces: Glabrous, with very glossy upper surface. Color of upper surface of young foliage: 143A with indistinguishable venation. Color of lower surface of young foliage: 143C with indistinguishable venation. Color of upper surface of mature foliage: NN137A with venation of 146A. Color of lower surface of mature foliage: 146B with venation of 146C.

*Petiole*.—Length: Approximately 2.0 mm. Diameter: Approximately 2.0 mm. Texture: Glabrous. Color: 144B.

Flowering description:

*Flowering season*.—Flowers in spring with intermittent flowering through fall.

*Lastingness of individual inflorescence on the plant*.—Approximately one week.

Flower description:

*General description*.—Type: Single, self-cleaning. Quantity per plant: Approximately 100. Fragrance: Strong, pleasantly sweet. Aspect: Upward to outward.

*Bud just before opening*.—Shape: Oblong. Length: Approximately 1.5 cm. Diameter: Approximately 1.0 cm. Color: 155B.

*Corolla*.—Shape: Rotate. Depth: Approximately 4.2 cm. Diameter: Approximately 4.5 cm.

*Corolla tube*.—Length: Approximately 4.0 cm. Diameter at distal end: Approximately 6.0 mm. Diameter at proximal end: Approximately 4.0 mm. Texture of inner and outer surfaces surface: Glabrous. Color of inner surface: 145C. Color of outer surface: 145B.

*Petals*.—Quantity: 6. Shape: Obovate. Margin: Entire, slightly undulate. Apex: Acute. Base: Truncate. Length: Approximately 2.0 cm. Width: Approximately 1.7 cm. Texture of upper and lower surfaces: Glabrous. Color of upper and lower surfaces when fully open: NN155C, fading to 8D.

*Calyx*.—Shape: Star-shaped. Depth: Approximately 2.0 cm. Diameter: Approximately 7.0 mm.

*Sepals*.—Quantity: 6. Shape: Narrow lanceolate. Margin: Entire. Apex: Acute. Base: Fused. Length: Approximately 1.1 cm. Width: Approximately 2.0 mm. Texture of upper surface: Glabrous. Texture of lower surface: Glabrous. Color of upper and lower surfaces: 144A.

*Peduncle*.—Strength: Strong. Shape: Rounded. Aspect: Erect to about 45° from branch axis. Length: Approximately 6.0 mm. Diameter: Approximately 3.0 mm. Texture: Glabrous. Color: 144A.

*Reproductive organs*.—Androecium: Stamen quantity per flower: 6. Anther shape: Narrow oblong, base is adnate to corolla. Anther length: Approximately 8.0 mm. Anther color: 161B. Pollen amount: Abundant. Pollen color: 14C. Gynoecium: Pistil quantity per flower: 1. Pistil length: Approximately 4.4 cm. Stigma shape: 3-lobed, globular. Stigma length: Approximately 1.0 cm. Stigma color: 6C. Style length: Approximately 3.1 cm. Style color: 4D. Ovary length: Approximately 3.0 mm. Ovary color: 3C.

Seed and fruit production: Neither seed nor fruit production has been observed.

Disease and pest resistance: Resistance to pathogens and pests common to *Gardenia* has not been observed.

What is claimed is:

1. A new and distinct cultivar of *Gardenia* plant named 'WAH-LM', substantially as herein illustrated and described.

* * * * *